(12) United States Patent
Joly et al.

(10) Patent No.: US 6,313,363 B1
(45) Date of Patent: *Nov. 6, 2001

(54) PROCESS FOR ISOMERIZING AROMATIC COMPOUNDS CONTAINING EIGHT CARBON ATOMS

(75) Inventors: Jean-François Joly, Lyons; Julia Magne-Drisch, Vilette de Vienne; Fabio Alario, Neully sur Seine; Elisabeth Merlen; Eric Benazzi, both of Chatou; Sylvie Lacombe, Rueil Malmaison, all of (FR)

(73) Assignee: Institut Francais du Petrole (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/289,655

(22) Filed: Apr. 12, 1999

Related U.S. Application Data

(60) Provisional application No. 60/096,863, filed on Aug. 18, 1998.

(30) Foreign Application Priority Data

Apr. 10, 1998 (FR) .................................................. 98 04651

(51) Int. Cl.$^7$ ........................................................ C07C 5/22
(52) U.S. Cl. ......................... 585/480; 585/481; 585/482; 585/906
(58) Field of Search ................................... 585/480, 481, 585/482, 906; 502/85, 86, 325, 326, 327, 332

(56) References Cited

U.S. PATENT DOCUMENTS

| | | | |
|---|---|---|---|
| 3,116,232 | 12/1963 | Nager | 208/64 |
| 3,409,685 | 11/1968 | Donaldson et al. | 260/668 |
| 3,409,686 | 11/1968 | Mitsche | 260/668 |
| 3,553,276 | 1/1971 | Berger | 585/482 |
| 3,577,475 | 5/1971 | Csicsery | 585/482 |
| 3,632,525 | 1/1972 | Rausch | 252/442 |
| 3,644,200 | * 2/1972 | Young | 208/120 |
| 3,748,255 | 7/1973 | Cassidy | 208/65 |
| 3,915,843 | 10/1975 | Franck et al. | 208/112 |
| 3,997,618 | * 12/1976 | Cornely et al. | 260/668 A |
| 3,998,900 | 12/1976 | Wilhelm | 585/379 |
| 4,062,903 | 12/1977 | Jacobson | 585/252 |
| 4,139,571 | 2/1979 | Riehm | 585/478 |
| 4,158,676 | 6/1979 | Smith et al. | 585/481 |
| 4,255,606 | 3/1981 | Tse | 585/482 |
| 4,593,138 | * 6/1986 | Casci et al. | 585/481 |
| 4,700,012 | 10/1987 | Onodera | 585/481 |
| 4,740,491 | 4/1988 | Wise et al. | 502/216 |
| 4,740,650 | 4/1988 | Pellet | 585/480 |
| 4,762,957 | 8/1988 | Sachtler | 585/481 |
| 4,983,558 | 1/1991 | Born et al. | 502/31 |
| 5,516,957 | 5/1996 | Dandekar | 585/482 |
| 6,057,486 | 5/2000 | Merlen et al. | 585/481 |
| 6,059,956 | 5/2000 | Dufresne | 208/108 |
| 6,147,269 | 11/2000 | Joly et al. | . |
| 6,198,014 | 3/2001 | Alario et al. | . |

FOREIGN PATENT DOCUMENTS

| | | |
|---|---|---|
| 051 318 | 5/1982 | (EP) . |
| 249 914 | 12/1987 | (EP) . |
| 0 335 754 | 10/1989 | (EP) . |
| 0 369 078 | 5/1990 | (EP) . |
| 0 490 696 | 6/1992 | (EP) . |
| 0 812 620 | 12/1997 | (EP) . |
| 2 209 827 | 7/1974 | (FR) . |
| 2 668 951 | 5/1992 | (FR) . |
| 851576 | 10/1960 | (GB) . |
| 50-16780 | * 6/1975 | (JP) . |
| 92/13046 | 8/1992 | (WO) . |
| 96/16004 | 5/1996 | (WO) . |

* cited by examiner

*Primary Examiner*—Marian C. Knode
*Assistant Examiner*—Thuan D. Dang
(74) *Attorney, Agent, or Firm*—Millen, White, Zelano & Branigan, P.C.

(57) ABSTRACT

The present invention relates to a process for isomerizing aromatic compounds containing 8 carbon atoms, the catalysts containing at least one group VIII metal, comprising at least one sulfurization step and at least one passivation step using ammonia.

7 Claims, No Drawings

PROCESS FOR ISOMERIZING AROMATIC COMPOUNDS CONTAINING EIGHT CARBON ATOMS

CROSS REFERENCE TO RELATED APPLICATIONS

This application claims the benefit of U.S. Provisional Application No. 60/096,863 filed Aug. 18, 1998.

The present invention relates to the field of processes for isomerising aromatic compounds containing eight carbon atoms.

In known processes for isomerising aromatic compounds containing eight carbon atoms, a feed which is relatively depleted in para-xylene with respect to the thermodynamic equilibrium of the mixture (i.e., where the para-xylene content is substantially lower than that of the mixture at thermodynamic equilibrium at the temperature under consideration, the mixture comprising at least one compound selected from the group formed by meta-xylene, ortho-xylene, para-xylene and ethylbenzene) and generally rich in ethylbenzene with respect to the same mixture at thermodynamic equilibrium, is introduced into a reactor containing at least one catalyst, under temperature and pressure conditions suitable for producing at the reactor outlet a composition containing aromatic compounds containing eight carbon atoms which is as close as possible to the mixture at thermodynamic equilibrium at the temperature of the reactor.

Para-xylene and possibly ortho-xylene, namely the desired isomers as they are of great importance in particular for the synthetic fibre industry, are then separated from that mixture. The meta-xylene and ethylbenzene can then be recycled to the isomerisation reactor inlet so as to increase the production of para-xylene and ortho-xylene. If ortho-xylene is not to be recovered, it is recycled with the meta-xylene and ethylbenzene.

However, there are a number of problems when isomerising aromatic compounds containing eight carbon atoms per molecule, caused by secondary reactions. Thus in addition to the main isomerisation reaction, hydrogenation reactions can be seen, such as hydrogenation of aromatic compounds to naphthenes, and naphthene ring opening reactions which lead to the formation of paraffins having at most the same number of carbon atoms per molecule as the naphthenes from which they originate. Cracking reactions are also observed, such as paraffin cracking reactions which lead to the formation of light paraffins typically containing 3 to 5 carbon atoms per molecule, also dismutation and transalkylation reactions which lead to the production of benzene, toluene, aromatic compounds containing 9 carbon atoms pre molecule (for example trimethylbenzenes) and heavier aromatic compounds.

The totality of such secondary reactions greatly reduces the yields of the desired products.

The quantity of secondary products formed (essentially naphthenes typically containing 5 to 8 carbon atoms, paraffins typically containing 3 to 8 carbon atoms, benzene, toluene, and aromatic compounds containing 9 to 10 carbon atoms per molecule) depends on the nature of the catalyst and the operating conditions of the isomerisation reactor (temperature, partial pressures of hydrogen and hydrocarbons, feed flow rate).

The skilled person is well aware that in some catalytic processes, catalyst activation and/or selectivisation procedures must be carried out to optimise the performances of the catalyst.

As an example in the case of a catalyst containing a metal from group VIII of the periodic table ("Handbook of Physics and Chemistry", $45^{th}$ edition, 1964–65), such as platinum, pre-treating the catalyst with hydrogen sulphide ($H_2S$) is well known. The sulphur contained in the hydrogen sulphide molecule becomes fixed on the metal and endows it with improved catalytic properties.

In conventional processes for isomerising aromatic compounds containing eight carbon atoms, a mixture of xylenes and ethylbenzene is brought into contact with a suitable catalyst, generally containing a noble group VIII metal and a zeolite, in order to bring the mixture of aromatic compounds containing eight carbon atoms to a composition which is as close as possible to the composition corresponding to thermodynamic equilibrium at the temperature under consideration.

SUMMARY OF THE INVENTION

The present invention concerns a process for activating catalysts for isomerising aromatic compounds containing eight carbon atoms comprising at least one sulphurization step and at least one passivation step using ammonia, carried out in any order, the sulphurization step normally being preceded by reduction of the metal compound contained in the catalyst.

The invention also concerns a process for isomerising aromatic compounds containing eight carbon atoms in which the catalyst used is activated, comprising at least one sulphurization step and at least one passivation step using ammonia, and an apparatus for carrying out the process.

We have discovered, surprisingly, that catalytic performances—in particular the para-xylene yield—are substantially improved in this type of catalyst when such catalysts are used in a pre-sulphurized or sulphurized form after introduction into the reactor and when they undergo passivation in the presence of ammonia ($NH_3$) or an ammonia precursor.

The process of the present invention has a number of advantages over the prior art, among them a reduction in the loss of aromatic compounds containing eight carbon atoms by side reactions of dismutation, transalkylation, hydrogenation and cracking. Further, carrying out the process of the present invention means that lower temperature and pressure conditions can be used with the catalyst, also higher HSVs (wt of feed/weight of catalyst/hour).

The procedure for activating the catalyst of the present invention is applicable to all catalysts for isomerising aromatic compounds containing eight carbon atoms which contain at least one metal or compound of a metal from group VIII selected from iron, cobalt, nickel, ruthenium, rhodium, palladium, osmium. indium and platinum, and preferably at least one noble metal or compound of a metal from group VIII, preferably selected from platinum and palladium, and optionally at least one metal or compound of a metal selected from metals or compounds of metals from groups IIIA and IVA.

The catalyst may contain a zeolite. In this case, the invention is of particular application to catalysts containing at least one zeolite with a mordenite, MFI, EUO or mazzite structure type such as omega zeolite.

More particularly, this activation procedure can be applied to a catalyst comprising at least one zeolite with structure type EUO, for example EU-1 zeolite. The zeolite with structure type EUO which is used contains silica and at least one element T selected from the group formed by aluminium, iron, gallium and boron, preferably aluminium and boron, and in which the global Si/T atomic ratio is about 5 to 100, preferably about 5 to 80, and more preferably about 5 to 60. More particularly, this activation process can be applied to a catalyst comprising at least one zeolite with structure type MOR. Zeolite with structure type MOR has an Si/Al ratio of less than 20, preferably in the range 5 to 15.

When the catalyst contains a zeolite, the zeolite represents a weight of 1% to 90%, preferably 3% to 60%, and more preferably 4% to 40% with respect to the total weight of the catalyst. The weight content of the group VIII element(s) is generally about 0.01% to 2.0% with respect to the total catalyst weight, preferably about 0.05% to 1.0% with respect to the total catalyst weight. This group VIII element is preferably selected from the group formed by platinum and palladium. The element is usually platinum. The catalyst can be formed using a matrix, in a content which forms the complement of 100% by weight of the catalyst.

When the catalyst used in the present invention is formed with a matrix, the matrix is generally selected from the group formed by natural clays (for example kaolin or bentonite), synthetic clays, magnesia, aluminas, silicas, silica-aluminas, titanium oxide, boron oxide, zirconia, aluminium phosphates, titanium phosphates, and zirconium phosphates, preferably from elements of the group formed by aluminas and clays. This matrix can be a simple compound or a mixture of at least 2 of these compounds.

In the particular case where the catalyst contains a zeolite, for example a zeolite with structure type EUO, the zeolite is at least in part, preferably practically completely, in its acid form, i.e., in its hydrogen form ($H^+$), the sodium content being such that the Na/T atomic ratio is less than 0.5, preferably less than 0.1.

The catalyst which is activated in accordance with the process of the invention also optionally contains at least one additional element selected from the group formed by elements from groups IIIA and IVA of the periodic table, preferably selected from the group formed by tin and indium. The weight content of these element(s) is generally about 0.01% to 2.0% with respect to the total catalyst weight, preferably about 0.05% to 1.0% with respect to the total catalyst weight.

The catalyst is sulphurized using a sulphur compound, for example hydrogen sulphide or a hydrogen sulphide precursor. The catalyst can be sulphurized before the catalyst is introduced into the reactor, in which case the catalyst is termed a "pre-sulphurized catalyst". It can also be carried out on a catalyst which is already in place in the reactor.

In general, before sulphurization, the group VIII metal compound contained in the catalyst is reduced. This pre-sulphurization step can be carried out using hydrogen sulphide, either pure or using a precursor, preferably an organic precursor, of hydrogen sulphide which is then decomposed in the reactor.

Non limiting examples of sulphur-containing organic compounds which can be used in the sulphurization step of the present invention are sulphur-containing alkyl compounds, sulphur-containing aryl compounds, and sulphur-containing alkylaryl compounds. Examples are butylethylsulphide, diallylsulphide, dibutylsulphide, dipropylsulphide, dimethyldisulphide (DMDS), thiophene, dimethylthiophene and ethylthiophene.

The catalyst sulphurization step is normally carried out in a neutral or reducing atmosphere at a temperature of about 20° C. to 500° C., preferably about 60° C. to about 400° C., at an absolute pressure of about 0.1 to 5 MPa, and preferably about 0.3 to 3 MPa, and with a gas volume (inert or reducing) per volume of catalyst per hour (HSV) of about 50 $h^{-1}$ to 600 $h^{-1}$, preferably about 100 $h^{-1}$ to 200 h1. The inert gas is usually nitrogen and the reducing gas is normally hydrogen, usually substantially pure hydrogen.

The sulphurization step is associated with a passivation step carried out in the presence of ammonia ($NH_3$). Passivation can be carried out before or after sulphurization. Preferably, the sulphurization step is carried out before the passivation step. These two sulphurization and passivation steps can be carried out before or after introducing the catalyst into the reactor. Preferably, passivation in the presence of ammonia is carried out when the catalyst is already in place in the reactor.

Passivation with ammonia is usually carried Out in two stages: injecting at least one defined quantity of ammonia in the form of $NH_3$ vapour or in the form of at least one ammonia precursor, then continuously injecting ammonia in the form of $NH_3$ vapour or in the form of at least one ammonia precursor during introduction of the feed to be isomerised. The injection duration for ammonia in the form of $NH_3$ vapour or ammonia precursor in the second stage depends on the start-up time for the catalyst, in particular it depends on temperature stabilisation in the catalyst. Preferably, the first injection is made with $NH_3$ in vapour form and the second injection is made with at least one ammonia precursor.

Ammonia ($NH_3$) precursors which can be used in the present invention are any compounds known to the skilled person which decompose in the presence of hydrogen to ammonia which becomes fixed on the catalyst. Examples of compounds which can be used are aliphatic amines such as n-butylamine.

In a preferred implementation of the present invention, the steps of sulphurization and passivation with ammonia are carried out after charging the catalyst into the reactor, the sulphurization step preferably preceding a catalyst reduction step.

When it is carried out, the catalyst is reduced in the presence of hydrogen, preferably with a purity of over 90 mole %. The reduction temperature is about 300° C. to 550° C., preferably about 400° C. to 520° C. The total pressure is in the range from atmospheric pressure to 3 MPa, preferably about 0.5 to 2 MPa. The reduction step normally lasts 1 to 40 hours, preferably about 1 to 8 hours.

The hydrogen flow rate (fresh hydrogen and hydrogen recycled from the outlet to the reactor inlet) is about 0.1 l/h/g to 100 l/h/g of catalyst.

When the catalyst is sulphurized in the presence of hydrogen, usually using hydrogen sulphide ($H_2S$) as the sulphurizing agent, a quantity of hydrogen sulphide corresponding to a weight content of about 0.01% to 0.8%, preferably about 0.01% to 0.5% with respect to the catalyst mass is introduced into the reactor. The temperature, pressure and hydrogen flow rate conditions are identical to those of the reduction step, but in contrast the hydrogen introduced into the reactor is preferably only recycled hydrogen.

Passivation with ammonia during the first stage of this passivation is carried out using gaseous ammonia or at least one ammonia precursor compound, in general mixed with hydrogen. The quantity of ammonia introduced into the reactor is about 0.02% to 5% by weight, preferably about 0.1% to 2% by weight with respect to the catalyst mass.

The temperature, pressure and hydrogen flow rate conditions are identical to those of the reduction step, but in contrast the hydrogen introduced into the reactor is preferably recycled hydrogen alone.

Once the sulphurization step and the first stage of the passivation step have been completed, the feed to be isomerised is introduced into the reactor, usually with an amine, preferably n-butylamine, in a quantity corresponding to about 20 ppm to 500 ppm by weight with respect to the catalyst mass. This introduction corresponds to the second stage of the passivation step.

The temperature and pressure conditions of the isomerisation reaction are selected so that maximum para-xylene production is encouraged. Addition of n-butylamine is stopped when the temperatures measured at different points of the catalytic bed or beds have stabilised.

The temperature of the isomerisation reaction in the presence of hydrogen is about 300° C. to 500° C., preferably about 320° C. to 450° C. and more preferably about 340° C. to 430° C., the partial pressure of hydrogen is about 0.3 to 1.5 MPa. preferably about 0.4 to 1.2 MPa, the total pressure is about 0.45 to 1.9 MPa. preferably about 0.6 to 1.5 MPa, the HSV (wt of feed/weight of catalyst/hour) is about 0.25 to 15 $h^{-1}$, preferably about 1 to 10 $h^{-1}$, and more preferably about 2 to 6 $h^{-1}$.

The process of the present invention is applicable to any catalyst suitable for carrying out isomerising a mixture of aromatic compounds containing eight carbon atoms per molecule.

These catalysts can be used in different implementations. In a preferred implementation of the isomerisation process of the present invention, at least one compound with a boiling point of about 80° C. to 135° C., more particular at least one compound selected from the group formed by paraffins containing eight carbon atoms per molecule, benzene, toluene, and naphthenes containing eight carbon atoms, is introduced with the feed to be isomerised and with the hydrogen required for the reaction.

The compound or compounds are added to the feed to be isomerised as a recycle, in the form of fresh compounds or in the form of a mixture of recycled compounds and fresh compounds in quantities such that the percentages by weight of the compounds added with respect to the total feed entering the reactor are normally as follows:

- the percentage by weight of paraffins containing eight carbon atoms, in the optional case where it is added to the feed, is about 0.1% to 10%, preferably about 0.2% to 2%;
- the percentage by weight of naphthenes containing eight carbon atoms, in the optional case where it is added to the feed, is about 0.5% to 15%, preferably about 2% to 8%;
- the percentage by weight of toluene, in the optional case where it is added to the feed, is about 0.1% to 10%, preferably about 0.2% to 5%;
- the percentage by weight of benzenes, in the optional case where it is added to the feed, is about 0.1% to 10%, preferably about 0.2% to 2%.

The percentage by weight of total compounds added, when a plurality of compounds are added, normally represents about 0.1 to 20% by weight, preferably about 2% to 15% by weight with respect to the total feed entering the isomerisation zone.

The following examples illustrate the invention without limiting its scope.

The following abbreviations are used in the examples of the present description: "C1–C8 paraffins" for paraffins containing 1 to 8 carbon atoms; "C5–C9 naphthenes" for naphthenes containing 5 to 9 carbon atoms; and "C9–C10 aromatics" for aromatic compounds containing 9 and 10 carbon atoms.

EXAMPLE 1
(In Accordance with the Invention)

The catalyst used in this example was prepared using the following procedure:

The starting zeolite was a mordenite in its sodium form, with an Si/Al ratio of 5.2 and a unit cell volume of 2.794 $nm^3$ (cubic manometers, i.e., 2794×$10^{-27}$ cubic metres). The zeolite underwent three ion exchanges in a solution of 10 N ammonium nitrate $NH_4NO_3$ solution at about 100° C. for 4 hours. The solid obtained contained 25 ppm of sodium.

This zeolite in its $NH_4^+$ form was then formed by extrusion with an alumina gel to obtain, after drying and calcining in dry air, a catalyst containing 15% by weight of mordenite zeolite in its hydrogen form and 85% of alumina.

This catalyst then underwent anion exchange with hexachloroplatinic acid in the presence of a competing acid (hydrochloric acid), to deposit 0.3% by weight of platinum with respect to the catalyst mass. The wet solid was dried at 120° C. for 12 hours and calcined in a stream of dry air at a temperature of 500° C. for 1 hour. The catalyst obtained contained 14.96% by weight of mordenite in its hydrogen form, 84.76% of alumina and 0.28% of platinum (expressed as platinum metal).

A reactor containing 60 g of mordenite based catalyst prepared as above was used.

After charging the catalyst, drying and reducing the metal compound contained in the catalyst at 450° C., a sulphurization step was carried out using hydrogen sulphide ($H_2S$) at a pressure of 16 bars absolute.

To effect sulphurization, a quantity of $H_2S$ equal to 0.1% by weight with respect to the catalyst mass was introduced, the temperature thus being 380° C.

After injecting $H_2S$, the reactor was maintained for 1 hour at 380° C. while recycling hydrogen without adding fresh hydrogen. The temperature of the reactor was then raised to 390° C., the temperature increase being made gradually over one hour. It then remained at 390° C., for two hours.

Before introducing the ammonia, the reactor temperature was gradually raised to 425° C., then this temperature was held for one hour.

The quantity of $NH_3$ injected was 0.25% by weight with respect to the catalyst mass. After injecting ammonia, the catalyst was left for 2 hours at 425° C. with a hydrogen recycle. The temperature of the reactor was then gradually reduced to 390° C., over a period of two hours.

The temperature was stabilised at 390° C., and a hydrogen flow rate of 10 nl/h (normal liters per hour) was established. The feed, with an added 0.034% by weight of n-butylamine, was then injected. The conditions for injecting the feed to be isomerised were as follows: a temperature of 390° C., an HSV of 3 $h^{-1}$ and a total pressure of 1.5 MPa.

The temperature evolution was measured using thermocouples located at different heights in the catalytic bed. Two thermocouples were located in the catalyst, these thermocouples being designated $TC_6$ and $TC_7$.

The maximum temperatures of the feed—attained 4 hours after injection—were $TC_6$=413° C. and $TC_7$=405.8° C.

The values of the temperatures measured by the two thermocouples $TC_6$ and $TC_7$ being stable, injection of n-butylamine was stopped 24 hours after starting injection of the feed.

The feed to be converted was a mixture of aromatic compounds containing eight carbon atoms, with a composition by weight shown in Table 1.

The operating conditions were as follows: a temperature of 380° C., a total pressure of 1.2 MPa and an HSV of 3 $h^{-1}$ (weight of feed/weight of catalyst/hour).

After 1028 hours, the composition of the effluent was measured; this composition is shown in Table 1.

TABLE 1

| Compounds | Feed (% by weight) | Effluent (% by weight) |
|---|---|---|
| C1–C6 paraffins | 0 | 1.20 |
| C5 to C9 naphthenes | 0 | 20.11 |
| Benzene | 0 | 0.13 |
| Toluene | 0 | 0.75 |
| Ethylbenzene | 14.39 | 6.69 |
| Para-xylene | 1.54 | 16.52 |
| Meta-xylene | 58.07 | 37.10 |
| Ortho-xylene | 26.00 | 16.50 |
| C9–C10 aromatic compounds | 0 | 1.00 |

EXAMPLE 2

(Comparative)

60 g of the same catalyst as that used in Example 1 was used. The reduction and suliphurization steps of Example 1 were identical. The ammonia passivation step was not carried out.

The same feed was used under the same operating conditions as in Example 1. The composition of the effluent after 1000 hours of operation is shown in Table 2.

TABLE 2

| Compounds | Feed (% by weight) | Effluent (% by weight) |
|---|---|---|
| C1–C6 paraffins | 0 | 1.67 |
| C5 to C9 naphthenes | 0 | 22.04 |
| Benzene | 0 | 0.14 |
| Toluene | 0 | 0.75 |
| Ethylbenzene | 14.39 | 6.48 |
| Para-xylene | 1.54 | 15.21 |
| Meta-xylene | 58.07 | 36.24 |
| Ortho-xylene | 26.00 | 16.06 |
| C9–C10 aromatic compounds | 0 | 1.41 |

The results shown in Tables 1 and 2 clearly demonstrate the importance of using the process of the present invention. Para-xylene production was greater, 16.52% by weight when the process of the invention was used as opposed to 15.21% by weight when the process was used without ammonia passivation of the catalyst.

The yield of aromatic compounds containing eight carbon atoms increased from 73.99% to 76.81% by weight when using the catalyst activation procedure of the present invention.

EXAMPLE 3

(In Accordance with the Invention)

The catalyst used in this Example was prepared as follows.

The starting material used was a zeolite with structure type EUO, zeolite EU-1, in its as synthesised form, comprising an organic structuring agent, silicon and aluminium, with an overall Si/Al atomic ratio of 13.6, and a sodium content with respect to the weight of dry EU-1 zeolite of about 1.5% by weight, corresponding to an Na/Al atomic ratio of 0.6.

This EU-1 zeolite first underwent dry calcining at 550° C. in a stream of air for 6 hours. The solid obtained then underwent three ion exchanges in a 10 N $NH_4NO_3$ solution at about 100° C. for 4 hours for each exchange.

After these treatments, the EU-1 zeolite in its $NH_4NO_3$ form had an overall Si/Al atomic ratio of 18.3, and a sodium content with respect to the weight of dry EU-1 zeolite of 50 ppm.

The EU-1 zeolite was then formed by extrusion with an alumina gel to obtain, after drying and calcining in dry air, a support S1 constituted by extrudates 1.4 mm in diameter, which contained 10% by weight of EU-1 zeolite in its H form and 90% of alumina.

The support S1 obtained then underwent anion exchange with hexachloroplatinic acid in the presence of a competing agent (hydrochloric acid), to introduce platinum into the catalyst. The wet solid was then dried at 120° C. for 12 hours and calcined in a stream of dry air at a temperature of 500° C. for one hour.

The catalyst obtained contained 10.0% by weight of EU-1 zeolite in its H form, 89.7% of alumina and 0.29% of platinum.

The same steps of sulphurization and ammonia passivation as those described in Example 1 were applied to the EU-1 based catalyst. The same feed was converted.

The feed injection conditions were those of Example 1.

The following conditions were applied over an operating period of 1850 hours for the catalyst,:

T=380° C.

Total pressure=0.9 MPa

HSV=3 $h^{-1}$

The composition of the feed and effluent are shown in Table 3.

TABLE 3

| Compounds | Feed (% by weight) | Effluent (% by weight) |
|---|---|---|
| C1–C6 paraffins | 0 | 0.39 |
| C5 to C9 naphthenes | 0 | 7.85 |
| Benzene | 0 | 0.09 |
| Toluene | 0 | 0.23 |
| Ethylbenzene | 14.39 | 10.74 |
| Para-xylene | 1.54 | 18.78 |
| Meta-xylene | 58.07 | 41.72 |
| Ortho-xylene | 26.00 | 19.91 |
| C9–C10 aromatic compounds | 0 | 0.29 |

EXAMPLE 4

(Comparative)

The same EU-1 based catalyst as that used in Example 3 was used, and the activation procedure was reproduced but without the ammonia passivation step.

The following conditions were applied over an operating period of 1800 hours for the catalyst,:

T=380° C.

Total pressure=0.9 MPa

HSV=3 $h^{-1}$

The composition of the feed and effluent are shown in Table 4.

TABLE 4

| Compounds | Feed (% by weight) | Effluent (% by weight) |
|---|---|---|
| C1–C6 paraffins | 0 | 0.56 |
| C5 to C9 naphthenes | 0 | 8.8 |
| Benzene | 0 | 0.18 |
| Toluene | 0 | 0.25 |
| Ethylbenzene | 14.39 | 10.79 |
| Para-xylene | 1.54 | 17.91 |
| Meta-xylene | 58.07 | 41.42 |
| Ortho-xylene | 26.00 | 19.71 |
| C9–C10 aromatic compounds | 0 | 0.38 |

Applying the start-up procedure of the invention led to a substantial gain in performances in the presence of a catalyst containing EU-1 zeolite. The isomerisation activity was higher, the para-xylene content in the effluent increased from 17.91% to 18.78%. The C8 aromatic compounds yield was also higher: 91.15% by weight compared with 89.83% by weight. The catalyst used in accordance with the present invention was substantially more selective.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above, and of corresponding French application 98/04651, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for isomerising an aromatic compound containing eight carbon atoms per molecule, wherein a catalyst undergoes an activation process by subjecting the catalyst to at least one sulphurization and at least one passivation using ammonia wherein the passivation comprises a first stage wherein the catalyst is brought into contact at least once with ammonia in the form of a gas or in the form of an ammonia precursor prior to the introduction of an isomerisation feed; the process comprising adding hydrogen and a recycle mixture to the isomerisation feed at a reactor inlet, isomerizing at least one reactant from the recycle mixture and/or feed catalyzed by the sulphated and passivated catalyst; said recycle mixture consisting essentially of compounds having a boiling point of about 80° C.—about 135° C. comprising at least one acyclic paraffin containing eight carbon atoms per molecule, at least one naphthene containing eight carbon atoms per molecule, benzene, and toluene, and being devoid of (a) aromatic hydrocarbons containing at least eight carbon atoms per molecule and (b) paraffinic hydrocarbons containing 1–7 carbon atoms per molecule; said recycle mixture being obtained, at least partially, by recycling a fraction separated from the resulting effluent leaving the isomerization reactor.

2. A process for isomerising an aromatic compound containing eight carbon atoms according to claim 1, wherein the percentage by weight of the paraffin containing eight carbon atoms added with respect to the total feed at the reactor inlet is about 0.1 to about 10.

3. A process for isomerising an aromatic compound containing eight carbon atoms according to claim 1, wherein the percentage by weight of a naphthene containing eight carbon atoms added with respect to the total feed at the reactor inlet is about 0.5 to about 15.

4. A process for isomerising an aromatic compound containing eight carbon atoms according to claim 1, wherein the percentage by weight of toluene added with respect to the total feed at the reactor inlet is about 0.1% to about 10%.

5. A process for isomerising an aromatic compound containing eight carbon atoms according to claim 1, wherein the percentage by weight of benzene with respect to the total feed at the reactor inlet is about 0.1% to about 10%.

6. A process for isomerising an aromatic compound containing eight carbon atoms according to claim 1, wherein at least one compound is added in a quantity or quantities such that the total percentage by weight of the compound or compounds added is about 0.1% to about 20%.

7. A process for isomerising an aromatic compound containing eight carbon atoms per molecule according to claim 1 comprising conducting the isomerising process at a temperature of about 300° C. to about 500° C., a partial pressure of hydrogen of about 0.3 MPa to about 1.5 MPa, a total pressure of about 0.45 MPa to about 1.9 MPa and a HSV of about 0.25 to about 15 $h^{-1}$.

* * * * *